United States Patent [19]

Chou

[11] 4,230,620
[45] Oct. 28, 1980

[54] PROCESS FOR PREPARING PENICILLIN SULFOXIDES

[75] Inventor: Ta S. Chou, Indianapolis, Ind.

[73] Assignee: Eli Lilly and Company, Indianapolis, Ind.

[21] Appl. No.: 23,875

[22] Filed: Mar. 26, 1979

[51] Int. Cl.³ ............................................. C07D 499/04
[52] U.S. Cl. ............................ 260/239.1; 260/245.2 R
[58] Field of Search .......................... 260/239.1, 245.2; 544/16, 22

[56] References Cited

U.S. PATENT DOCUMENTS

| 3,197,466 | 7/1965 | Chow et al. | 260/239.1 |
| 3,544,581 | 12/1970 | Essery | 260/239.1 X |
| 3,586,667 | 6/1971 | Hatfield | 260/239.1 |
| 4,052,387 | 10/1977 | Kukolja | 544/22 |
| 4,081,440 | 3/1978 | Kukolja | 544/22 X |

OTHER PUBLICATIONS

Kennedy et al., *J. Org. Chem.*, 25, 1905–1906, (1960).
Chow et al., *J. Org. Chem.*, 27, 1381–1383, (1962).
Barton et al., *J. Am. Chem. Soc.*, 91, 1529–1530, (1969).
Cooper et al., *J. Am. Chem. Soc.*, 91, 1408–1415, (1969).
Spry, *J. Am. Chem. Soc.*, 92, 5006–5008, (1970).
Spry, *J. Org. Chem.*, 37, 793–795, (1972).

*Primary Examiner*—Natalie Trousof
*Assistant Examiner*—Vera C. Clarke
*Attorney, Agent, or Firm*—William C. Martens, Jr.; Arthur R. Whale

[57] ABSTRACT

A penicillin is treated with a peroxymonosulfate at a temperature of from about 0° C. to about 50° C. in an aqueous medium to produce a penicillin sulfoxide.

12 Claims, No Drawings

PROCESS FOR PREPARING PENICILLIN SULFOXIDES

BACKGROUND OF THE INVENTION

This invention relates to a process for oxidizing a penicillin to a penicillin sulfoxide. Depending upon the position of the oxygen of the sulfoxide moiety, penicillin sulfoxides can exist in either the α- or the β- form. These can be depicted as follows:

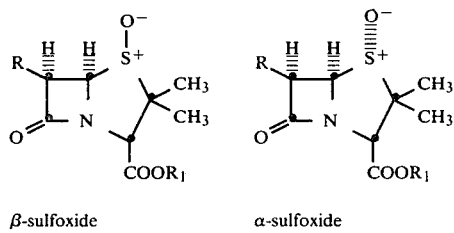

β-sulfoxide          α-sulfoxide

The literature recognizes several methods for oxidizing a penicillin to its penicillin sulfoxide. In most instances, these methods achieve production of the β-sulfoxide with little or no production of the α-sulfoxide. The typical recognized oxidation methods can be grouped as follows:

(1) Use of peracids

These methods involve treatment of the penicillin with a peracid, such as m-chloroperbenzoic acid or peracetic acid. The peracetic acid can be formed in situ from a mixture of hydrogen peroxide and acetic acid. In every case, the only sulfoxide which is formed has the β-configuration. These methods are described in publications such as, for example, Cooper et al., *J. Am. Chem. Soc.* 91, 1408 (1969), and Barton et al., *J. Am. Chem. Soc.* 91, 1529 (1969).

(2) Use of hydrogen peroxide

This method achieves only a very low level of conversion and produces exclusively the β-sulfoxide. The extent of conversion can be potentiated by incorporation of a catalyst, for example, sodium tungstate. This method is referred to in Japanese Pat. No. 91087/73.

(3) Use of ozone

A penicillin can be oxidized to a mixture of the α- and β-sulfoxides by treatment with ozone. Although this method permits production of the α-sulfoxide in addition to the β-sulfoxide, it suffers by reason of the fact that, in order to achieve any substantial α-sulfoxide formation, a very dilute aqueous system is required. This precludes any practical application of the ozone oxidation process in production of α-sulfoxide. Moreover, the α-sulfoxide which is recovered from the ozone process is a relatively impure and amorphous material which requires additional crystallization treatments with attendant product loss. Spry, *J. Am. Chem. Soc.*, 92, 5006 (1970) describes this method.

A process has now been discovered which permits oxidation of penicillins to produce penicillin sulfoxides in highly pure form, and, in many cases, substantial quantities of the penicillin α-sulfoxide. It is to such a process that this invention is directed.

SUMMARY OF THE INVENTION

Therefore, this invention is directed to a process for oxidizing a penicillin to a penicillin sulfoxide, said penicillin having the formula

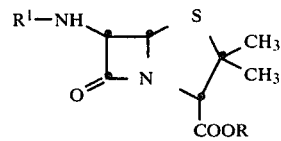

in which $R^1$ is selected from the group consisting of phenoxyacetyl, benzoyl, thienyl-2-acetyl, phenylglycyl, and hydrogen; and R is selected from the group consisting of hydrogen, an alkali metal cation, and a carboxylic acid protecting group; which comprises contacting said penicillin in an aqueous medium at a temperature of from about 0° C. to about 50° C. with a peroxymonosulfate.

DETAILED DESCRIPTION OF THE INVENTION

As indicated above, this invention is directed to a process for oxidizing a penicillin to its corresponding α- and β-sulfoxides. The penicillin starting material employed in the process of this invention has the formula

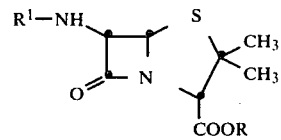

in which the group $R^1$ is phenoxyacetyl, benzoyl, thienyl-2-acetyl, phenylglycyl, or hydrogen. As a highly preferred embodiment of this invention, the penicillin starting material is one in which $R^1$ is phenoxyacetyl.

As noted, $R^1$ can be hydrogen or phenylglycyl. When $R^1$ is either of these, a free amino group is defined. This amino group must be protected during the course of the oxidation. Such protection can be achieved by simple conversion to an acid addition salt, and, since the conditions of oxidation in accordance with the process of this invention are acidic, an acid addition salt will normally automatically be formed under the conditions of reaction. Typical salts include hydrochloride, sulfate, p-toluenesulfonate, and the like. In addition, the amino group can be protected by use of one of the commonly employed amino blocking groups such as t-butyloxycarbonyl, benzyloxycarbonyl, 4-methoxybenzyloxycarbonyl, 4-nitrobenzyloxycarbonyl, 2,2,2-trichloroethoxycarbonyl, and the like. Additional typical amino protecting groups are described by J. W. Barton in *Protective Groups in Organic Chemistry*, J. F. W. McOmie, Ed., Plenum Press, New York, N.Y., 1973, Chapter 2.

The group R in the above formula is hydrogen, an alkali metal cation, or a carboxylic acid protecting group. Preferably, the group R is an alkali metal cation, such as sodium or potassium, and, when R is hydrogen, the penicillin is solubilized by conversion to its alkali metal salt either during or prior to the oxidation. When R is a carboxylic acid protecting group, it preferably is one which is removable by acid treatment or by hydrogenation.

The term "carboxylic acid protecting group", when employed herein, preferably refers to an ester moiety, in particular, one of those groups commonly employed to block or protect the carboxyl group of a compound while a reaction or sequence of reactions involving other functional sites are carried out. Such carboxylic acid protecting groups are noted for their ease of cleavage to produce the corresponding carboxylic acid by hydrolytic or by hydrogenolytic methods. Preferred carboxylic acid protecting groups include, for example, $C_1$-$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, dimethylallyl, phenacyl, and p-halophenacyl, in any of the above of which halo denotes chlorine, bromine, or iodine. The nature of such protecting group is not critical so long as the ester formed therewith is stable under the reaction conditions of the process of this invention. Furthermore, other known carboxylic acid protecting groups such as those described by E. Haslam in *Protective Groups in Organic Chemistry*, supra, Chapter 5, are considered to be within the term "carboxylic acid protecting group" as used herein.

Specific illustrations of highly preferred carboxylic acid protecting groups present on the penicillins used in the process of this invention include, for example, t-butyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like. Most preferred carboxylic acid protecting groups are t-butyl, benzyl, p-nitrobenzyl, p-methoxybenzyl, benzhydryl, and 2,2,2-trichloroethyl.

The oxidation of the penicillin to the corresponding sulfoxide, and, generally, to a mixture of the corresponding $\alpha$- and $\beta$-sulfoxides, is carried out using a peroxymonosulfate salt as oxidizing agent, and, typically, an alkali metal peroxymonosulfate, such as sodium peroxymonosulfate, potassium peroxymonosulfate, and the like. A highly useful such agent is commercially available under the trade name Oxone®. Oxone® is a peroxymonosulfate composition having the formula $$2KHSO_5 \cdot KHSO_4 \cdot K_2SO_4$$

Several of the oxidative uses of Oxone® have been reported in the paper by R. J. Kennedy and A. M. Stock, *Journal of Organic Chemistry*, 25, 1901 (1960). This paper describes the oxidation of a wide variety of compounds including two sulfur-containing compounds, dodecyl mercaptan and diphenyl sulfide, to produce dodecylsulfonic acid and diphenyl sulfone, respectively. The process of this invention provides the first instance in which a peroxymonosulfate has been applied to the oxidation of a penicillin, with the accompanying discovery that the oxidation (1) can be stopped at the intermediate sulfoxide oxidation state, (2) can be carried out without disruption of the penicillin structure, and (3) can in many instances be used to produce substantial quantities of the hitherto difficulty obtainable penicillin $\alpha$-sulfoxide.

In order to avoid over-oxidation of the penicillin to the penicillin sulfone, the peroxymonosulfate preferably is used in an amount representing that which provides active oxygen in an amount not exceeding about 35% over that required to achieve oxidation of all of the penicillin starting material to the penicillin sulfoxide. More preferably, the excess is in the range of from about 2% to about 10%. Of course, substantially greater amounts of the peroxymonosulfate can be used with accompanying formation of varying amounts of the over-oxidation product. Conversely, substantially lesser amounts of the peroxymonosulfate can be used resulting, of course, in oxidation of only a portion of the penicillin starting material.

The oxidation is carried out in the presence of water in an amount at least sufficient to completely dissolve the peroxymonosulfate oxidizing agent. Moreover, when the group R of the penicillin starting material is hydrogen or an alkali metal cation, water is used generally in an amount sufficient to dissolve both the peroxymonosulfate and the penicillin, and, furthermore, when R is hydrogen, a base, such as sodium or potassium hydroxide, is added to render the penicillin soluble in the aqueous medium.

In addition, it is highly preferred to include, as part of the aqueous medium, a water-miscible organic solvent. When the group R in the penicillin starting material is a carboxylic acid protecting group, it is necessary, in order to dissolve the penicillin, to include a suitable quantity of such water-miscible organic solvent. Nevertheless, the use of a water-miscible organic solvent in the process of this invention is highly preferred irrespective of the particular definition of the group R. Typical water-miscible organic solvents include, for example, acetone, methyl ethyl ketone, acetonitrile, and the like. Of these, the most preferred is acetone. In general the volume ratio of water to the organic solvent is from about 1:4 to about 6:1.

In general, the pH of the reaction mixture during oxidation will be in the range of from about 2 to about 6. Under the conditions of reaction, this pH range normally will automatically result and be maintained throughout. However, the pH can be controlled within the more desirable range of from about 3.3 to about 5, and, preferably, from about 3.5 to about 4.5, by periodic or continuous addition during the course of the oxidation of a buffer, such as an alkali metal hydroxide, for example, potassium or sodium hydroxide.

The penicillin and the peroxymonosulfate, dissolved together in the aqueous medium, are allowed to react at a temperature within the range of from about 0° C. to about 50° C. The ratio of the $\alpha$-sulfoxide product to the $\beta$-sulfoxide product generally can be increased by carrying out the oxidation at a temperature in the upper portion of the foregoing range, for example, from about 30° C. to about 50° C.

The ratio of $\alpha$-sulfoxide to $\beta$-sulfoxide can also be increased by addition of a small amount of a salt of a metal selected from the group consisting of molybdenum, tungsten, and vanadium. The amount of the added salt generally ranges from about 0.5% to about 10% and, preferably, from about 1% to about 5%, by weight, relative to the penicillin starting material. Typical salts include sodium tungstate dihydrate ($Na_2WO_4 \cdot 2H_2O$), molybdenum dioxy acetylacetonate [$MoO_2(AcAc)_2$], vanadium monoxy acetylacetonate [$VO(AcAc)_2$], and the like.

A typical generalized procedure illustrating the process of this invention is as follows:

Appropriate quantities of a salt of 6-phenoxyacetamido penicillin acid and the peroxymonosulfate oxidizing agent are dissolved in a mixture of acetone and water. The oxidation is allowed to proceed at the selected temperature in the range of about 0°–50° C. In the acetone-water medium, the resulting $\beta$-sulfoxide product crystallizes from the reaction mixture upon formation whereas the $\alpha$-sulfoxide product remains in solution. Upon completion of the oxidation, the $\beta$-sulfoxide product is filtered from the mixture. Ethyl acetate then is added to the filtrate which contains the α-sulfoxide product. The ethyl acetate layer is separated from the aqueous layer and concentrated with accompanying crystallization and recovery of the penicillin α-sulfoxide product.

The penicillin sulfoxides such as are produced by the process of this invention have long been recognized as useful intermediates in the production of antibiotically active cephalosporins.

For example, Kukolja, in U.S. Pat. No. 4,081,440, describes the conversion of 6-acylamino penicillin sulfoxides to the acylamino 2-chlorosulfinylazetidin-4-one compounds by treating the former with an N-chloro halogenating agent, such as N-chlorophthalimide, in the presence of an alkylene oxide, such as propylene or butylene oxide.

In a related patent, U.S. Pat. No. 4,052,387, Kukolja describes a process for converting acylamino 2-chlorosulfinylazetidin-4-ones by Lewis acid-Friedel-Crafts catalyzed intramolecular cyclization to the 7-acylamino-3-exomethylenecepham-4-carboxylic acid sulfoxides, which, in turn, are useful in preparing antibiotically active cephalosporins.

Moreover, Chou, in co-pending Application Ser. No. 829,689 filed Sept. 1, 1977, and now U.S. Pat. No. 4,159,272 issued June 26, 1979, describes an enhancement of the foregoing Kukolja sequence by producing the 2-chlorosulfinylazetidin-4-one intermediate from a 6-acylamino-2,2-dimethylpenam-3-carboxylic acid sulfoxide in which the sulfoxide group has the α-configuration.

Thus, the process of this invention provides compounds which are highly useful in the foregoing sequence and, in particular, since the process of this invention in many instances permits production of substantial quantities of the α-sulfoxide, is highly useful in the foregoing improved process described by Chou in co-pending application Ser. No. 829,689.

The following examples are provided to illustrate the process of this invention. They are not intended to be limiting on the scope thereof.

EXAMPLE 1

To 75 ml. of acetone were added 4.85 grams (10 millimoles) of p-nitrobenzyl 6-phenoxyacetamido-2,2-dimethylpenam-3-carboxylate. To the resulting solution were added 10 ml. of water. A solution of 4.0 grams of Oxone ® (13 millimoles active oxygen) in 20 ml. of water was slowly added dropwise at room temperature over a 15 minute period to the penicillin ester solution. A precipitate formed immediately upon addition of the Oxone ® solution. The mixture was stirred an additional 15 minutes. Water (20 ml.) then was added, and the mixture was filtered. The collected solid was dried in vacuo at room temperature to obtain 4.9 grams (97%) of p-nitrobenzyl 6-phenoxyacetamido-2,2-dimethylpenam-3-carboxylate-1β-oxide ($R_f$=0.47, as indicated by thin-layer chromatography in a 3:1 mixture of toluene and acetonitrile) containing a small amount of starting material ($R_f$=0.71).

NMR (DMSO-$d_6$): δ 1.20 (s, 3H, C-2 methyl), δ 1.63 (s, 3H, C-2 methyl), δ 4.65 (s, 2H, side chain CH$_2$), δ 5.40 (s, 2H, ester CH$_2$), δ 5.50 (d, 1H, C-5 H, J=4.5 cps), δ 6.00 (d, 1H, C-6H, J=4.5 and 9 cps), δ 6.83–7.42 (m, 5H, C$_6$H$_5$O—), and δ 7.67 and 8.28 (2d, 4H, O$_2$N—C$_6$H$_4$—, J=9 cps).

The mother liquor was extracted with ethyl acetate (75 ml.), dried over magnesium sulfate, and filtered. The organic layer was evaporated in vacuo on a rotary evaporator. Thin layer chromatography of the residue indicated predominately p-nitrobenzyl 6-phenoxyacetamido-2,2-dimethylpenam-3-carboxylate-1α-oxide with a small amount of the β-sulfoxide and starting material.

EXAMPLE 2

To 50 ml. of water were added 19.4 grams (50 millimoles) of the potassium salt of 6-phenoxyacetamido-2,2-dimethylpenam-3-carboxylic acid. A solution of 20 grams (65 millimoles active oxygen) of Oxone ® in 100 ml. water was added dropwise to the penicillin solution over a 45 minute period. The mixture was stirred for about 10 minutes at room temperature. The resulting precipitate was collected by filtration and washed with 25 ml. of water. The precipitate was dried in vacuo at 40° C. overnight to afford 17.95 grams (98%) of the corresponding penicillin sulfoxide. Analysis of the product by high performance liquid chromatography (HPLC) indicated the presence of 23.0% of the α-isomer and 74.1% of the β-isomer.

The NMR spectrum also indicated that the product was a 3:1 (β:α) mixture of the two sulfoxide isomers. The NMR (DMSO-$d_6$) of the two isomers had the following features which were used to estimate the α to β ratio.

| isomer | $C_3$—H | N—H |
| --- | --- | --- |
| α | δ4.30 | δ9.37 |
| β | δ4.42 | δ8.32 |

The signals for the $C_3$ protons were singlets, which rendered them extremely useful in estimating the α:β ratio.

EXAMPLE 3

To a mixture of 300 ml. of water and 100 ml. of acetone were added 43.7 grams (0.1 mole) of the potassium salt of 6-phenoxyacetamido-2,2-dimethylpenam-3-carboxylic acid. The solution was heated to 50° C. in a hot water bath, and a solution of 40.0 grams (0.13 mole active oxygen) of Oxone ® in 200 ml. of water was added dropwise over a period of 21 minutes, the temperature of the mixture being maintained at 50° C. During addition of the Oxone ® solution, a 1 N potassium hydroxide solution was added dropwise at a rate sufficient to maintain the pH at 3.5–3.6. A total of 170 ml. of the aqueous potassium hydroxide solution was added. Upon completion of addition of the Oxone ® solution, 100 ml. of acetone were added. Upon addition of the acetone, the β-sulfoxide product precipitated from the mixture. The resulting mixture containing the precipitate was stirred at 50° C. for 10 minutes and then was cooled to room temperature in a cold-water bath during which time 9.4 ml. of concentrated sulfuric acid were added to complete crystallization. The pH of the resulting mixture was 1.7. The mixture was filtered, and the collected precipitate was dried in vacuo to afford 29.1 grams (79.5%) of the β-sulfoxide product moderately contaminated by accompanying inorganic materials.

NMR (DMSO-$d_6$): δ 1.25 (s, 3H, C-2 methyl), δ 1.62 (s, 3H, C-2 methyl), δ 4.42 (s, 1H, C-3 H), δ 4.63 (s, 2H, side chain CH$_2$), δ 5.48 (d, 1H, C-5 H, J=4.5 cps), δ 5.97

(q, 1H, C-6 H, J=4.5, 10 cps), δ 6.83–7.47 (m, 5H, C$_6$H$_5$O—) and δ 8.23 (d, 1H, —NH—, J=10 cps).

The filtrate was extracted twice with 250 ml. of ethyl acetate. The ethyl acetate was dried over magnesium sulfate and evaporated to about 20–25 ml. The mixture was refrigerated overnight. The product was collected by filtration and dried in vacuo to afford 9.1 grams (24.9%) of the α-sulfoxide isomer, m.p. 157°–158° C.

NMR (DMSO-d$_6$): δ 1.23 (s, 3H, C-2 CH$_3$), δ 1.57 (s, 3H, C-2 CH$_3$), δ 4.30 (s, 1H, C-3 H), δ 4.61 (s, 2H, side chain CH$_2$), δ 4.73 (d, 1H, C-5 H, J=4.5 cps), δ 5.47 (q, 1H, C-6 H, J=4.5 cps and 8 cps), δ 6.73–7.50 (m, 5H, C$_6$H$_5$O—) and δ 9.37 (d, NH, J=8 cps).

EXAMPLE 4

To a mixture of 300 ml. of water and 100 ml. of acetone were added 43.7 grams (100 millimoles) of the potassium salt of 6-phenoxyacetamido-2,2-dimethylpenam-3-carboxylic acid. The solution was heated to 50° C. in a hot water bath. A separate solution of 40.0 grams (130 millimoles active oxygen) of Oxone ® in 200 ml. of water was prepared. To the Oxone ® solution was added 0.33 gram (1 millimole) of sodium tungstate dihydrate. The resulting mixture, a white, milky suspension, was added dropwise over a 21 minute period to the penicillin solution maintained at 50° C. A 1 N aqueous potassium hydroxide solution was added dropwise along with the Oxone ® solution at a rate sufficient to maintain the pH at 3.5–3.6 A total of 185 ml. of the potassium hydroxide solution was added, the pH upon completion being 3.6. Upon completion of the addition, 100 ml. of acetone were added. The mixture was stirred at 50° C. for 10 minutes and then was cooled to room temperature over a 15 minute period in a cold water bath with accompanying addition of 10.3 ml. of concentrated sulfuric acid. The pH of the resulting mixture was 1.6. The mixture was filtered, and the collected precipitate was dried in vacuo at 40° C. to afford 23.7 grams (64.8%) of the β-sulfoxide isomer product.

NMR (DMSO-d$_6$): δ 1.25 (s, 3H, C-2 CH$_3$), δ 1.62 (s, 3H, C-2 CH$_3$), δ 4.40 (s, 1H, C-3 H), δ 4.62 (s, 2H, side chain CH$_2$), δ 5.48 (d, 1H, C-5 H, J=4.5 cps), δ 5.97 (q, 1H, C-6 H, J=4.5, 10 cps), δ 6.83–7.47 (m, 5H, C$_6$H$_5$O—) and δ 8.23 (d, —NH—, J=10 cps).

The filtrate was extracted twice with 250 ml. of ethyl acetate. The ethyl acetate was dried over magnesium sulfate and evaporated to about 20–25 ml. The mixture was filtered, and the collected precipitate was dried in vacuo to afford 11.05 grams (30.2%) of the α-sulfoxide isomer product.

NMR (DMSO-d$_6$): δ 1.23 (s, 3H, C-2 CH$_3$), δ 1.57 (s, 3H, C-2 CH$_3$), δ 4.30 (s, 1H, C-3 H), δ 4.61 (s, 2H, side chain CH$_2$), δ 4.73 (d, 1H, C-5 H, J=4.5 cps), δ 5.47 (q, 1H, C-6 H, J=4.5 cps and 8 cps), δ 6.73–7.50 (m, 5H, C$_6$H$_5$O—) and δ 9.37 (d, NH, J=8 cps).

EXAMPLE 5

To 20 ml. of water were added 2.16 grams (10 millimoles) of 6-amino-2,2-dimethylpenam-3-carboxylic acid. The resulting suspension had a pH of 3.2. To the resulting suspension then was added over a 10 minute period at room temperature a solution of 3.1 grams (10 millimoles active oxygen) of Oxone ® in 20 ml. of water. The suspension cleared after approximately one-half of the Oxone ® solution had been added. The resulting mixture had a pH of 1.4. To the mixture then were added 10 millimoles of p-toluenesulfonic acid, and the resulting mixture was evaporated to about one-tenth volume to obtain a crystalline precipitate. The precipitate was removed by filtration to obtain 1.0 gram of the p-toluenesulfonate salt of 6-amino-2,2-dimethylpenam-3-carboxylic acid 1β-oxide.

EXAMPLE 6

To 150 ml. of water were added 11.6 grams (110 millimoles) of sodium carbonate followed by 100 ml. of acetone. To the mixture then were added portion-wise 10.8 grams (50 millimoles) of 6-amino-2,2-dimethylpenam-3-carboxylic acid. The resulting suspension was stirred for about one hour with formation of an almost clear solution. The mixture then was cooled to 2° C., pH 10.2. Benzoyl chloride (6.4 ml.; 55 millimoles) was added dropwise over a 9 minute period (pH 7.4) followed by dropwise addition over a 5 minute period of 16.9 grams of Oxone ® in 80 ml. of water. A 6° C. exotherm was noticed. The resulting suspension was stirred in an ice bath for 1 hour. The pH of the resulting mixture was 7.0. Concentrated hydrochloric acid (9 ml.) was added to pH 2.0, and the mixture was extracted twice with ethyl acetate. The organic layer was dried over sodium sulfate and evaporated to dryness. A small amount of ethyl acetate was added to the residue, and the product was allowed to crystallize overnight at room temperature to afford 11.6 grams (69%) of 6-benzamido-2,2-dimethylpenam-3-carboxylic acid 1-oxide.

IR (KBr): 1800, 1750, 1680 and 1665 cm$^{-1}$.

Analysis, Calculated for C$_{15}$H$_{16}$N$_2$O$_5$S: C, 53.56; H, 4.79; N, 8.33; O, 23.78; S, 9.53. Found: C, 53.35; H, 4.96; N, 8.06; O, 23.77; S, 9.34.

EXAMPLE 7

To a 150 gallon stirred, jacketed tank were added a solution of 17.66 kg. (40 moles; purity 88%) of potassium 6-phenoxyacetamido-2,2-dimethylpenam-3-carboxylate in 35 liters of water. To the solution then were added 80 liters of water, 40 liters of acetone, and 132 grams of sodium tungstate dihydrate. The mixture, having a pH of 7.3, was heated to 50° C. To the mixture then were added, at approximately 4.3 liters per minute, a solution of 16.0 kg. of Oxone ® in 80 liters of water. A 1 N aqueous potassium hydroxide solution was added along with the Oxone ® solution at a rate to maintain the pH of the resulting mixture between 4.2 and 4.7. The total addition time was 20 minutes during which the temperature was maintained at 48°–52° C. and the pH at 4.1–4.6. The pH of the final mixture was 4.5. Acetone (40 liters) then was added to the reaction mixture maintained at 50° C. The mixture was cooled to 25° C., and 21.1 liters of 20% sulfuric acid were added. The pH of the final mixture was 1.55. The mixture was filtered to afford 10.32 kg. of 6-phenoxyacetamido-2,2-dimethylpenam-3-carboxylic acid 1β-oxide contaminated with about 15% inorganic impurities. The yield of the β-sulfoxide was about 60% of theoretical.

The filtrate was extracted successively with 80 liters, 40 liters, and 40 liters of ethyl acetate. The ethyl acetate extracts were combined and concentrated in vacuo to a volume of about 23 liters at a temperature not exceeding about 40° C. The concentrate was cooled at 0° C. overnight, and 2.62 kg. (18%) of 6-phenoxyacetamido-2,2-dimethylpenam-3-carboxylic acid 1α-oxide were recovered by filtration. A second crop of the α-sulfoxide (1.17 kg.; 8%) was recovered from the filtrate, providing an overall yield of α-sulfoxide of about 26% of theory. This, coupled with the 60% β-sulfoxide product, constitutes a total yield of the penicillin sulfoxide product of about 86% of theory.

I claim:

1. A process for oxidizing a penicillin to a penicillin sulfoxide, said penicillin having the formula

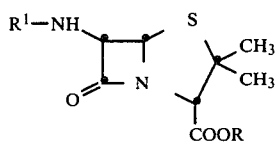

in which $R^1$ is selected from the group consisting of phenoxyacetyl, benzoyl, thienyl-2-acetyl, phenylglycyl, and hydrogen; and R is selected from the group consisting of hydrogen, an alkali metal cation, and a carboxylic acid protecting group; which comprises contacting said penicillin in an aqueous medium at a temperature of from about 0° C. to about 50° C. with a peroxymonosulfate under conditions such that the pH of the resulting mixture is maintained within the range from about 2 to about 6.

2. Process of claim 1, in which the peroxymonosulfate has the formula $2KHSO_5 \cdot KHSO_4 \cdot K_2SO_4$.

3. Process of claim 2, in which $R^1$ is phenoxyacetyl.

4. Process of claim 3, in which R is an alkali metal cation.

5. Process of claim 4, in which the aqueous medium contains a water miscible organic solvent selected from the group consisting of acetone, acetonitrile, and methyl ethyl ketone.

6. Process of claim 5, in which the water miscible organic solvent is acetone.

7. Process of claim 6, in which the oxidation is carried out at a temperature of from about 30° C. to about 45° C.

8. Process of claim 7, in which the oxidation is carried out in the presence of a salt of a metal selected from the group consisting of molybdenum, vanadium, and tungsten.

9. Process of claim 8, in which the salt is selected from the group consisting of sodium tungstate, molybdenum dioxy acetylacetonate, and vanadium monoxy acetylacetonate.

10. Process of claim 9, in which the salt is sodium tungstate.

11. Process of claim 10, in which the salt is present in an amount, relative to the penicillin starting material, from about 0.5% to about 10% by weight.

12. Process of claim 1, in which the peroxymonosulfate is present in an amount sufficient to generate active oxygen in an amount of from about 2% to about 10% excess of that required to account for total oxidation of the penicillin starting material to penicillin sulfoxide.

* * * * *